United States Patent
Dunlop

(10) Patent No.: US 9,308,122 B2
(45) Date of Patent: Apr. 12, 2016

(54) PATIENT WARMING SYSTEM

(76) Inventor: Colin Dunlop, East Ryde (AU)

( * ) Notice: Subject to any disclaimer, the term of this patent is extended or adjusted under 35 U.S.C. 154(b) by 1033 days.

(21) Appl. No.: 13/262,610

(22) PCT Filed: Apr. 1, 2010

(86) PCT No.: PCT/AU2010/000383
§ 371 (c)(1),
(2), (4) Date: Dec. 15, 2011

(87) PCT Pub. No.: WO2010/111750
PCT Pub. Date: Oct. 7, 2010

(65) Prior Publication Data
US 2012/0109269 A1   May 3, 2012

(30) Foreign Application Priority Data

Apr. 1, 2009  (AU) ............................... 2009901413
Jun. 18, 2009  (AU) ............................... 2009902819

(51) Int. Cl.
*A61F 7/08* (2006.01)
*A61D 3/00* (2006.01)
*A61F 7/00* (2006.01)

(52) U.S. Cl.
CPC ... *A61F 7/08* (2013.01); *A61D 3/00* (2013.01); *A61F 7/0097* (2013.01); *A61F 7/086* (2013.01); *A61F 2007/006* (2013.01); *A61F 2007/0091* (2013.01)

(58) Field of Classification Search
CPC ..... A01K 1/033; A61F 7/08; A61F 2007/006; A61F 2007/0062; A61F 2007/0091
USPC .................................. 607/104, 107; 119/500
See application file for complete search history.

(56) References Cited

U.S. PATENT DOCUMENTS

| | | | |
|---|---|---|---|
| 5,632,769 A | 3/1997 | Kappel et al. | |
| 5,975,025 A * | 11/1999 | Kangas et al. | ............... 119/484 |
| 6,014,949 A * | 1/2000 | Ball | ............... 119/484 |
| 2005/0279286 A1 * | 12/2005 | Youngmark | ............... 119/28.5 |
| 2006/0052851 A1 | 3/2006 | Anderson et al. | |
| 2007/0244533 A1 | 10/2007 | Pierre et al. | |
| 2008/0060586 A1 | 3/2008 | Lewis, Jr. et al. | |
| 2008/0288034 A1 | 11/2008 | Pierre et al. | |
| 2009/0143844 A1 * | 6/2009 | Cazzini | ............... 607/104 |

(Continued)

FOREIGN PATENT DOCUMENTS

| | | |
|---|---|---|
| CN | 201341688 Y | 11/2009 |
| WO | WO 00/04853 A1 | 2/2000 |
| WO | WO 00/04854 | 2/2000 |

OTHER PUBLICATIONS

ISR for International Application No. PCT/AU2010/000383 dated Jun. 11, 2010.
IPRP for International Application No. PCT/AU2010/000383 dated Jul. 20, 2011.

(Continued)

*Primary Examiner* — Kaitlyn Smith
(74) *Attorney, Agent, or Firm* — Knobbe, Martens, Olson & Bear, LLP

(57) ABSTRACT

The present invention relates to a system for keeping a patient warm, particularly a veterinary patient, during care. An apparatus is provided for delivering conditioned air across a barrier, such as a wire cage, to a blanket arrangement for providing conditioned air to the patient. A first duct and a second duct part are provided either side of the barrier mounted together across the barrier, so a duct is provided for ducting conditioned air across the barrier.

12 Claims, 10 Drawing Sheets

(56) References Cited

U.S. PATENT DOCUMENTS

| | | | |
|---|---|---|---|
| 2009/0248120 A1 | 10/2009 | Starr et al. | |
| 2010/0211139 A1 | 8/2010 | Pierre et al. | |
| 2011/0307038 A1* | 12/2011 | Stiehr et al. | 607/104 |
| 2012/0006280 A1* | 1/2012 | Gray | 119/500 |
| 2012/0109269 A1* | 5/2012 | Dunlop | 607/104 |

OTHER PUBLICATIONS

Combined Search and Examination in United Kingdom App. No. GB1317618.5, dated Nov. 5, 2013.

Patent Examination Report No. 1 in Australian App. No. 2010230859, dated Mar. 20, 2015.

Examination Report in United Kingdom App. No. GB1118890.1, dated Mar. 12, 2013.

* cited by examiner

PATIENT WARMING SYSTEM

FIELD OF THE INVENTION

The present invention relates generally to a system for keeping a patient warm during care and, more particularly, to an apparatus for delivering conditioned air across a barrier and a blanket arrangement for providing conditioned air to the patient, particularly, but not exclusively, for use in veterinary care.

BACKGROUND OF THE INVENTION

There are many circumstances in human and animal medicine where it is necessary to keep a patient warm to, for example, prevent or treat hypothermia. Forced warm air heating systems have been designed to keep patients warm during surgery and during critical care (e.g. recovery post-surgery).

Forced warm air heating systems were originally designed for use in human medicine only, for the prevention and treatment of hypothermia during anaesthesia and in critical care. Primarily, the blankets were placed over patients recovering from anaesthesia. Recently blankets have been designed to provide warm air heating for animals during surgery and recovery (see the applicant's earlier International Patent Application No. PCT/AU2003/001626, the disclosure of which is incorporated herein by reference).

Forced warm air heating systems usually comprise a blanket-type arrangement which comprises at least two layers forming a hollow space between them when air is delivered to the space. The blanket or a portion of the blanket may include one or more air holes or it may be of a porous/permeable material, to allow warmed air through the blanket to warm the patient. For small animals, blankets of or having a portion of permeable/porous material are preferred so that the warm air is diffused over the surface of the material (for example, the design disclosed in applicant's earlier PCT application No. PCT/AU2003/001626).

Forced warm air heating systems also include a heating unit for providing the warmed air, and a conduit, which may be in the form of a hose and/or pipe for delivering the warmed air from the heating unit to the blanket arrangement.

Animal patients during critical care or recovery (e.g. post anaesthesia) are usually caged for their restraint and safety (semi-conscious animals move about and can become injured through misadventures such as falling off treatment tables). Where an animal needs to be warmed during care, in the cage, this leads to a problem in using warmed air heating systems. The heater (with an electricity supply and heating unit, etc) must be placed outside the cage and any blanket arrangement must obviously be placed in the cage. There is therefore difficulty in providing the warm air conduit from the heater to the patient through the cage. The cage door must be properly shut so that the animal can't fall out. This problem is exacerbated by the fact that there are many different types of cages provided for veterinary patients, which, for example, have different diameters of bars, different grill patterns or grill widths for the cage and cage doors. These problems prevent currently available hoses/piping providing heating conduits from being able to pass through a cage or cage door into a cage.

Presently available warm air blanket arrangements typically have only one port by which warm air can enter the blanket (via the conduit). Generally, it is not convenient for the blanket to be moved once the patient is in the cage. Having only one port, say at the head of the blanket, may make it difficult for the warm air to be provided to the blanket without moving it. Having the port at the head end of the blanket (which is usually the case) in many cases, does not provide a convenient position for introducing the warmed air conduit to the port when the blanket arrangement is positioned within a cage.

Cages for animals in veterinary establishments are usually of a form having a solid bottom, ceiling and sides (which may be of metal or wood) and then one or two barred doors on the front of the cage, which swing fully open. As discussed above, trying to pass warmed air from a forced warmed air heating system via a conduit into the cage is difficult. The only option may be the cage door, which presents the further difficulty that the cage door must be able to be opened, sometimes quickly for urgent access.

SUMMARY OF THE INVENTION

In accordance with a first aspect, the present invention provides an apparatus for facilitating delivery of conditioned air across a barrier to a blanket arrangement providing the conditioned air to a patient, the apparatus comprising a first duct part, a second duct part and a mounting mechanism, the mounting mechanism arranged to mount the first duct part on one side of the barrier and the second duct part on the other side of the barrier opposite the first duct part, to provide a duct for ducting conditioned air across the barrier.

In an embodiment, the apparatus is arranged to duct air from a conduit providing the conditioned air to a further conduit on the other side of the barrier providing the conditioned air to the blanket arrangement. In an embodiment, the first part includes a first connector portion for releasably connecting to the conduit. In an embodiment, the second part comprises a second connector portion for connecting to the further conduit. The first connector portion may comprise a socket connector. The second connector portion may comprise a socket connector.

In an embodiment, the further conduit is integral with the blanket arrangement. In an embodiment, the further conduit is formed by the walls of a port to the interior of the air space of the blanket for receiving conditioned air.

In an embodiment, the apparatus further comprises a seal arrangement for sealing the duct across the barrier. In an embodiment, the sealing arrangement comprises a first seal portion mounted by the first part and a second seal portion mounted by the second part, the first and second seal portions arranged to make a seal across the barrier when the first and second parts are mounted on opposite sides of the barrier.

In another embodiment, the sealing arrangement comprises a seal portion mounted by the first or second part (not by both). The seal portion makes a seal across the barrier between the first and second parts.

In an embodiment, the mounting mechanism comprises a fastening mechanism for fastening the first and second parts to each other across the barrier. In an embodiment, the first part comprises a first flange and the second part comprises a second flange, arranged to be mounted opposite to each other.

In an embodiment, the barrier is part of a cage for holding the patient. In an embodiment, the part of the cage comprises bars or a mesh. In an embodiment, the part of the cage comprises a door of a cage.

In an embodiment, the patient is an animal patient.

In an embodiment, the invention has the advantage that air can be ducted across a barrier such as a barred or wire cage, for example, without any concern for the distance between the bars or the wire or the mesh. The arrangement ducts the air across the barrier, advantageously without having to change the width of the ducting. In an embodiment, where the apparatus may be mounted on a cage door, it has the further advantage that the cage door can be opened or closed without interfering substantially with the ducting of the air.

In accordance with a second aspect, the present invention provides a system for providing conditioned air to a patient, comprising an apparatus in accordance with the first aspect of the invention, and a blanket arrangement for receiving the conditioned air and providing it to the patient.

In an embodiment, the blanket arrangement includes a pervious surface through which conditioned air may pass to the patient. In an embodiment, the pervious surface is a permeable surface.

In accordance with an embodiment, the system further provides a conduit for providing conditioned air to the apparatus for facilitating and delivering the conditioned air across a barrier, and a further conduit for delivering the conditioned air to the blanket arrangement.

In an embodiment, the further conduit is formed by the walls of a port to the interior air space of the blanket arrangement.

In an embodiment, the system further comprises a conditioning unit for providing conditioned air to the conduit. In an embodiment, the conditioning unit is a heater for providing warmed air.

In an embodiment, the barrier is a part of a cage, and the system further comprises the cage.

In accordance with a third aspect, the present invention provides a blanket arrangement for delivering conditioned air to a patient, the blanket arrangement comprising at least two layers capable of forming an air space between them for receiving conditioned air, at least one of the two layers having at least a portion of its surface being pervious so that the conditioned air may be delivered to the patient, and a plurality of ports to the interior of the two layers, each of the ports being able to receive a part of a conduit for conducting conditioned air to the air space.

In an embodiment, the blanket arrangement has at least two corners, and a port is provided in each of the corners.

In an embodiment, the portion of the surface being pervious is one side of the blanket arrangement, another side of the blanket arrangement being impervious.

In an embodiment, the blanket is substantially square or rectangular.

In an embodiment, the blanket is sized to fit in a patient receiving space. In an embodiment, the patient receiving space is the floor of a veterinary cage.

In an embodiment, the ports are directed at an angle of between 30 and 50 degrees to the longitudinal axis of the blanket arrangement.

In another embodiment, the ports are directed in the same line as the length of the blanket arrangement, parallel to the longitudinal axis of the blanket arrangement.

In another embodiment, the ports are directed transversely to the length of the blanket arrangement, at approximately 90° to the blanket arrangement.

In an embodiment, the blanket arrangement of the invention may have the advantage that, because it has a plurality of ports, the blanket may be positioned in any configuration within, for example, an animal cage, and it can still be easily connected to a conduit for delivering warmed air, for example. Further, in the embodiment where the ports are angled, motion of a conduit connected to one of the ports, e.g. when a cage door is opened, may not effect a large movement of the blanket, so that the blanket advantageously stays substantially in position within the cage.

In an embodiment, there may be more than two ports.

In accordance with a fourth aspect, the present invention provides a blanket arrangement for delivering conditioned air to a patient, the blanket arrangement comprising at least two layers capable of forming an air space between them for receiving conditioned air, at least one of the two layers having at least a portion of its surface being pervious so that the conditioned air may be delivered to the patient, and at least one port to the interior of the two layers, the port being able to receive a part of a conduit for conducting conditioned air to the air space, the port being directed at an angle to the longitudinal axis of the blanket arrangement.

In an embodiment, the angle is between 30° and 50° to the longitudinal axis.

In an embodiment, the angle is approximately 90° to the longitudinal axis.

In an embodiment, there are a plurality of ports.

In accordance with a fifth aspect, the present invention provides a system, comprising a blanket arrangement in accordance with the fourth aspect or the third aspect of the invention, and an apparatus in accordance with the first aspect of the invention.

In accordance with a sixth aspect, the present invention provides a method of facilitating delivery of conditioned air across a barrier to a blanket arrangement providing the conditioned air to a patient, comprising the steps of ducting the air via the barrier.

BRIEF DESCRIPTION OF THE DRAWINGS

Features and advantages of the present invention will become apparent from the following description of embodiments thereof, by way of example only, with reference to the accompanying drawings, in which.

DETAILED DESCRIPTION OF EMBODIMENTS

Figure 1:
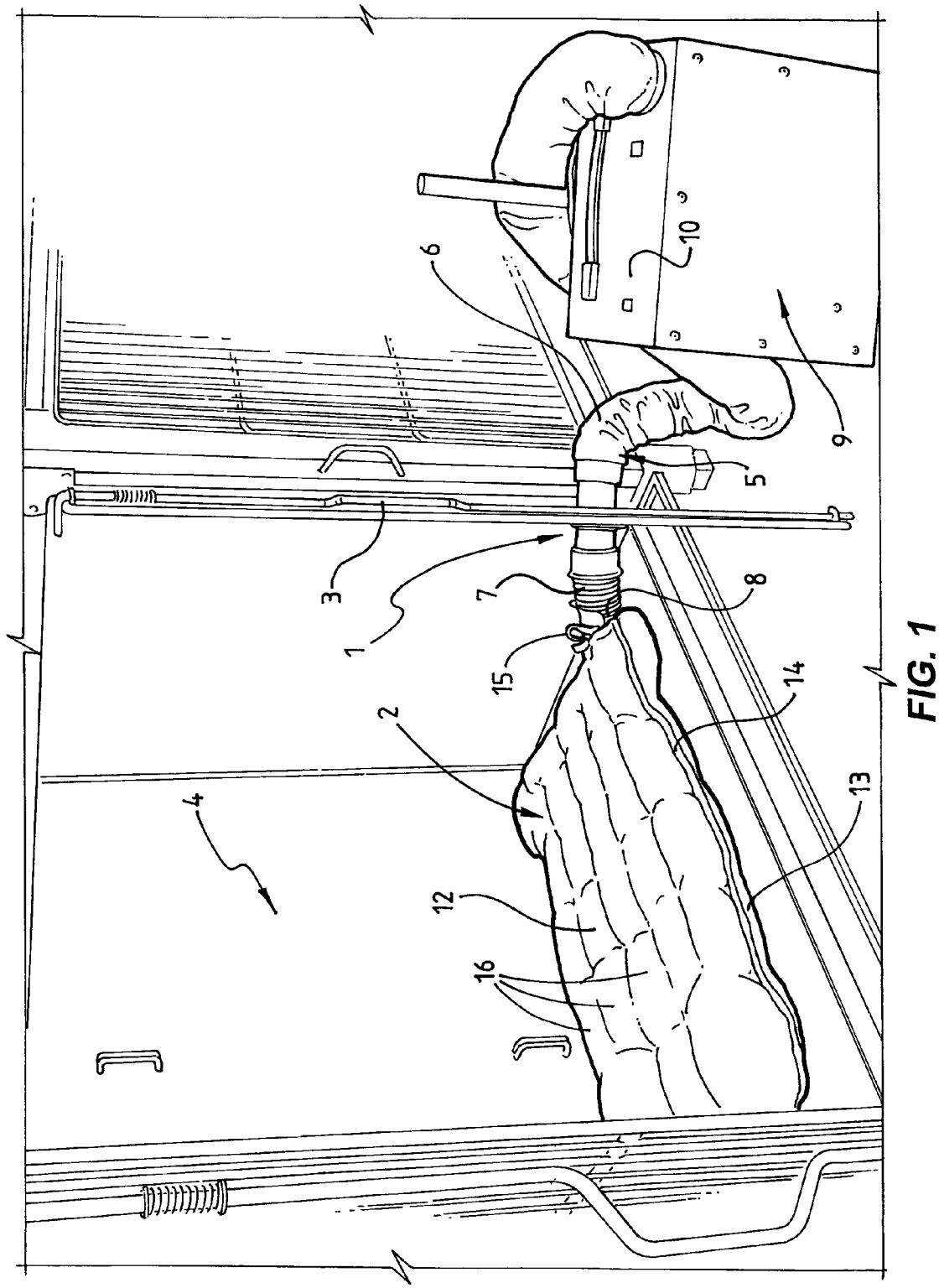
FIG. 1 is a picture of warmed air heating system for a patient, in accordance with an embodiment of the present invention.

A system for providing conditioned air to a patient, in accordance with an embodiment of the present invention, is shown in FIG. 1.

This embodiment comprises an apparatus, generally designated by reference numeral 1 for facilitating delivery of conditioned air (in this example warmed air) across a barrier to a blanket arrangement, generally designated by reference numeral 2. In this example embodiment, the barrier is the door 3 of a cage 4 arranged for containing an animal patient being treated. For example, the patient may be recovering from anaesthesia or surgery, or may be otherwise undergoing critical care.

In this embodiment, the system comprises a conduit 5 for delivering warmed air to the blanket 2. The conduit 5 comprises a conduit part 6, outside the cage 4 and further conduit part 7 mounted inside the cage 4 and connecting to the blanket 2 via port 8. In this example, the apparatus 1 effectively connects the conduit part 6 and further conduit part 7 to facilitate delivering of air to the blanket 2.

The system further comprises, in this embodiment, a heater unit 9 for providing warmed air.

The heating unit 9 includes controls 10 that enable a selection of a number of temperatures for the warmed air. For example warmed air may be delivered at temperatures of 34, 37, 40, 43 or 46 degrees centigrade.

The blanket arrangement 2, comprises two layers 12 and 13 bonded together at a seam 14. In this embodiment, the upper layer 12 is of non-pervious material, and the lower layer 13 is of a permeable material, allowing air to diffuse through it to warm the patient. In an embodiment the blanket may be made from polyester, the second layer 13 being of a porous polyester material. This is similar to the blanket disclosed in the applicant's earlier PCT application, number PCT/AU2003/001626.

In operation, the blanket 2 may be put over the patient or under the patient, so that warmed air is delivered via the porous material layer 13.

Animals undergoing post anaesthesia recovery or critical care are caged for their restraint and to permit observation and treatment, and for safety (semi-conscious animals move about and can become injured through misadventures). As can be seen from FIG. 1, the cage 4 shown is of a common type, with solid floor, ceiling and walls, and barred doors 3 that open outwards to enable access to the entire interior of the cage 4. The doors 3 of such cages must be properly shut so that the animal can't fall out.

Where warm air is being introduced to keep an animal in the cage warm, this obviously leads to an issue of how the warmed air is conveyed from the heater unit 9 through the barrier of the door bars to the interior of the cage and the blanket arrangement.

There are many animal cage manufacturers worldwide all using different designs and, for example, different diameters of steel rod, different grill patterns or grill widths for their cage doors. This further exacerbates the problem. The typical spacing between a vertical grill is 25 to 35 millimeters. This typical width is not sufficient to enable the conduit of typical warming systems to get through (the conduit is typically 60 millimeters or so in diameter).

Another issue is that it is obviously important to be able to open the doors easily and quickly to obtain access to the patient, which sometimes must be done urgently. The cage door must be able to swing open and access to the patient be unobstructed. At this time a hand may be needed to restrain the patient so it doesn't climb or fall out.

Another issue is that the warming conduit might be required to be moved quickly between cages to suit patient needs or from the right or left side of the cage depending on patient position and application.

All this is difficult with current air warming systems and conduits.

Another issue is that the warm air blanket 2 inside the cage should not be disturbed when the door shuts, so that it remains appropriately positioned over (or under) the patient. With current blankets, a port is provided in one position only (usually in the centre of the shorter side of the blanket). This position may not be ideal to the blanket remaining undisturbed when the cage door is closed and the conduit is moved. Further, the blanket may need to be set up on top of the patient, underneath the patient, or to the left or right of the cage, and with only one conduit (current blankets) access via only one port is difficult.

Figure 2:
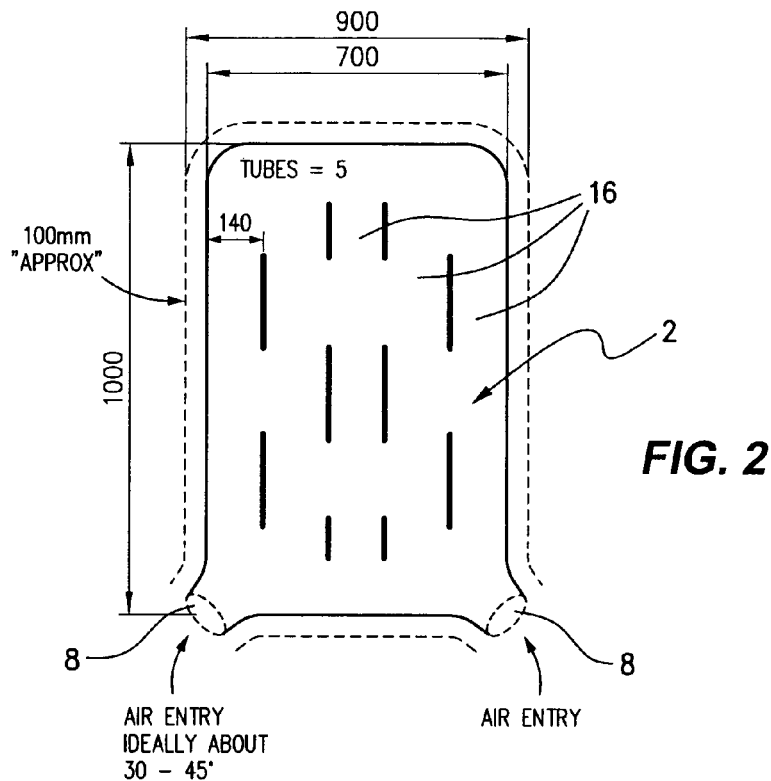
FIG. 2 is a diagram of a blanket arrangement in accordance with an embodiment of the present invention.

FIG. 2 shows an embodiment of a blanket in accordance with the present invention, which is pictured in FIG. 1. The blanket 2 comprises a plurality of ports 8, in this embodiment one port 8 at each bottom corner of the blanket 2. This allows ease of access by the conduit part 7 of the heating conduit 5, whether the blanket is used with the porous surface 13 downwards or the porous surface 13 upwards. The two ports 8 allow the conduit part 7 to be connected to the blanket 2 close to the cage door 3 in either configuration.

The ports 8 are also angled at about 30 to 50 degrees (preferably around about 45 degrees) to facilitate ease of access by the conduits 7. That is, the ports 8 are angled to the longitudinal direction of the blanket 2. This facilitates the blanket 2 remaining stationary when the cage door 3 is opened and shut, so the blanket is not disturbed from its position with respect to the patient. This also enables the blanket to be positioned over or under the patient with the cage door opened and the conduit 7 attached to the port.

Note that the ports 8 have a tie 15 which is used to secure the port 8 to the conduit 7.

The angled entry port 8 "softens" the effect of moving the inlet tube 7 through 90 degrees (cage door going from closed to open or vice versa), and the blanket 2 has minimal movement.

Advantageously, the features of the plurality of ports allows the blanket 2 to be used over the patient or under the patient and also the ports can be directed to either end of the cage so that the blanket can be used substantially in any configuration with respect to the cage 4.

The blanket 2 has a plurality of longitudinally extending air tubes 16. In this embodiment there are five longitudinally extending air tubes 16. If the blanket is positioned below the animal, for example, the animal may occlude some air tubes but not completely obstruct air flow.

Dimensions are given in millimeters of the blanket of the embodiment of FIG. 2. The blanket of FIG. 2 is arranged particularly to suit dog cages.

Figure 3:
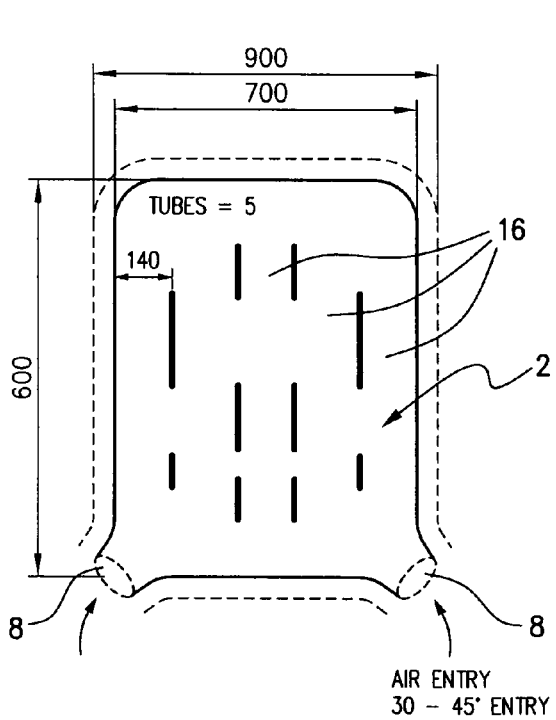
FIG. 3 is a diagram of a blanket arrangement in accordance with a further embodiment of the present invention.

The blanket of FIG. 3 has similar features to the embodiment of FIG. 2, and similar reference numerals have been used. The only thing that is different is the size. This blanket has been developed to suit cat cages.

It will be appreciated that the blanket arrangement can be made any size and it is not limited to those sizes illustrated in the drawings. It can be made any size suitable for any such patient or cage.

Figure 5:
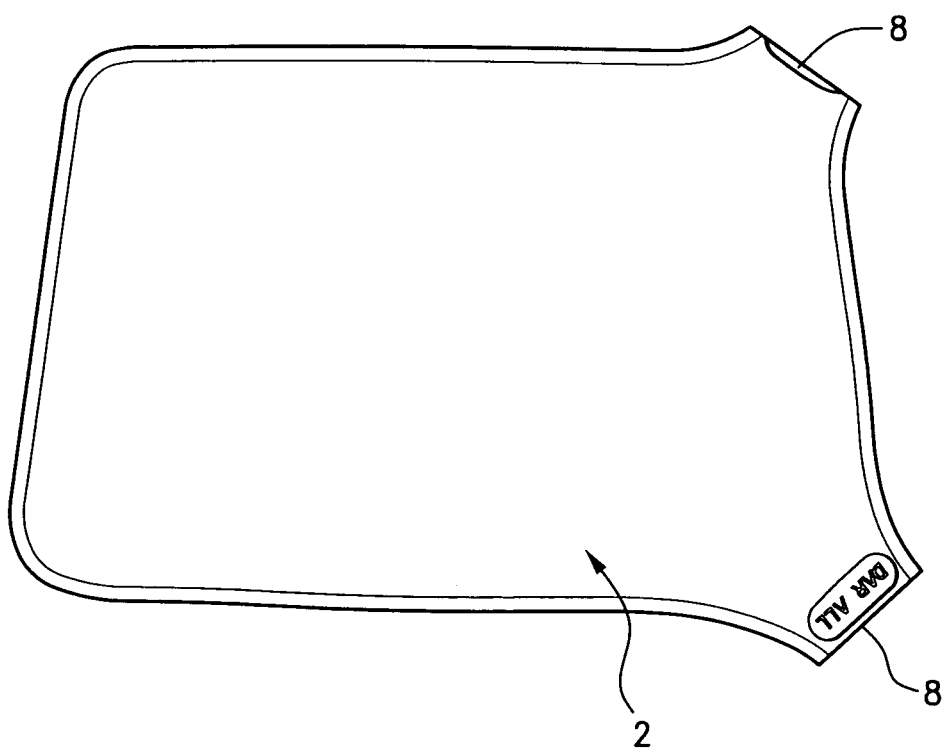
FIG. 5 is a picture of the blanket arrangement of the embodiment of FIG. 3.
Figure 6:
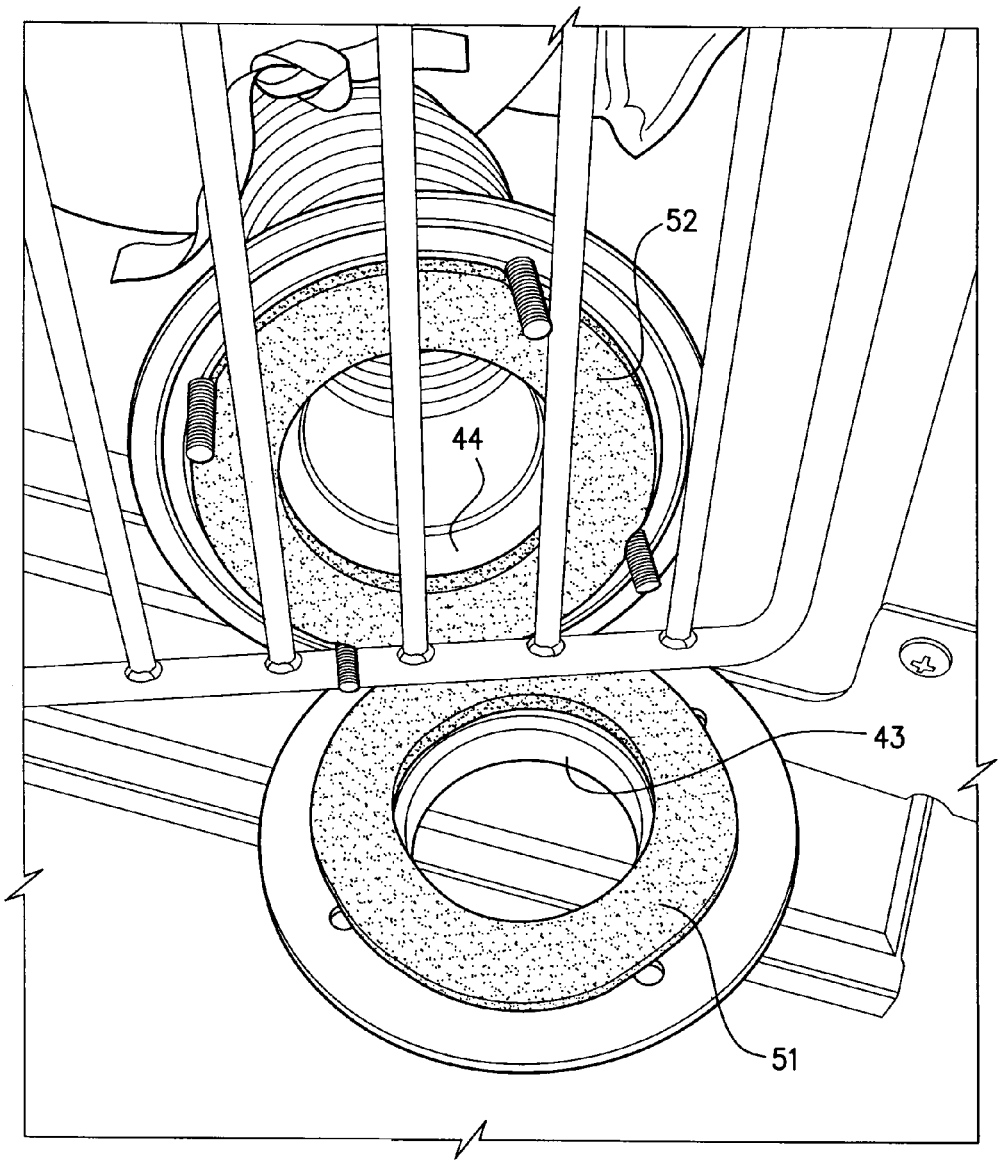
FIG. 6 is a view of an apparatus for facilitating delivery of conditioned air across a barrier, in accordance with an embodiment of the present invention, showing a first and second part of the embodiment being separated.
Figure 7:
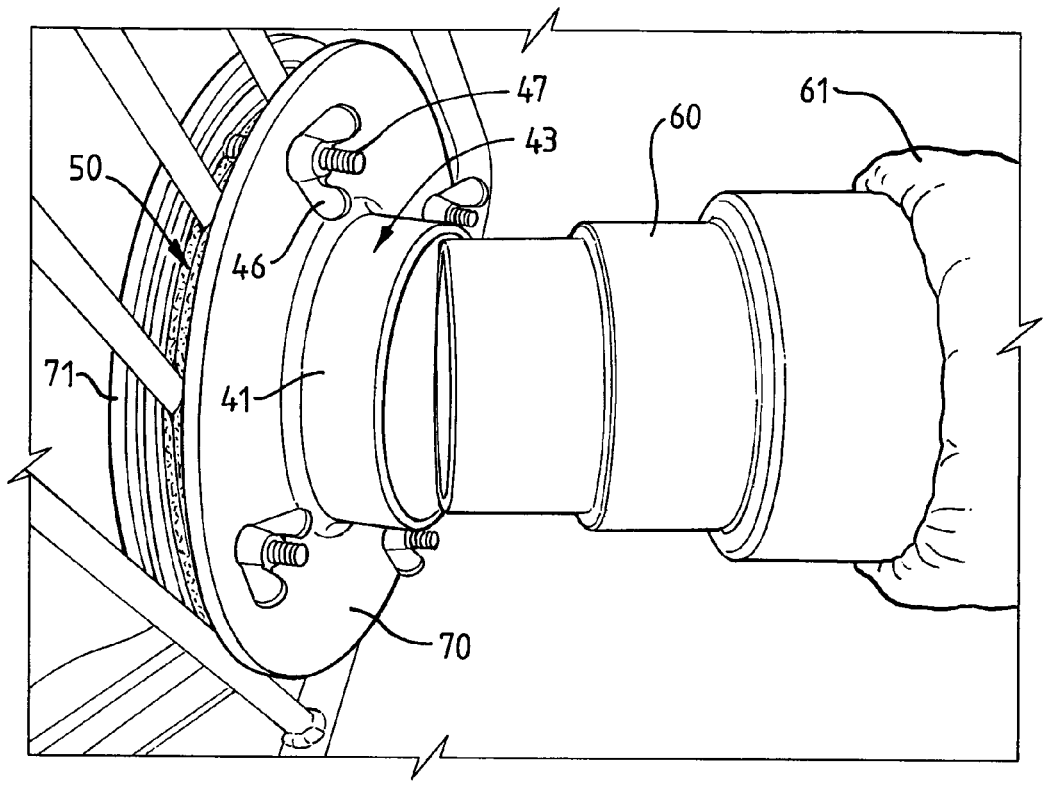
FIG. 7 is a further view of the apparatus of FIG. 6, where a first and second part of the apparatus are mounted either side of the barrier.
Figure 8:
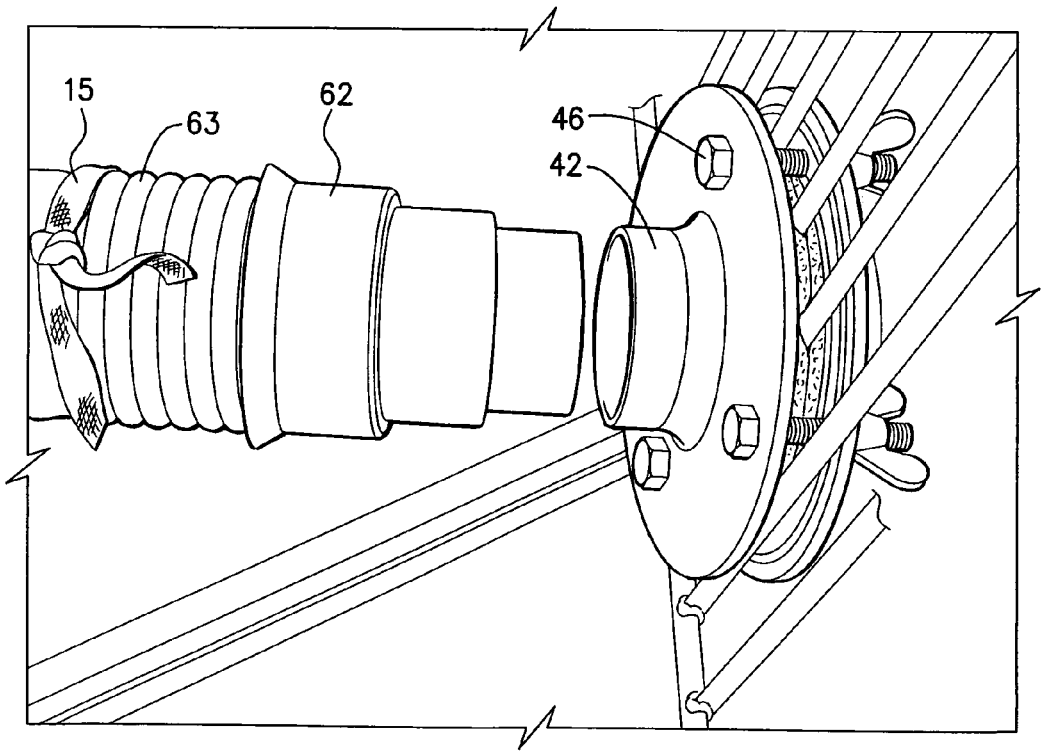
FIG. 8 shows a further view of the apparatus of FIG. 7.
Figure 9:
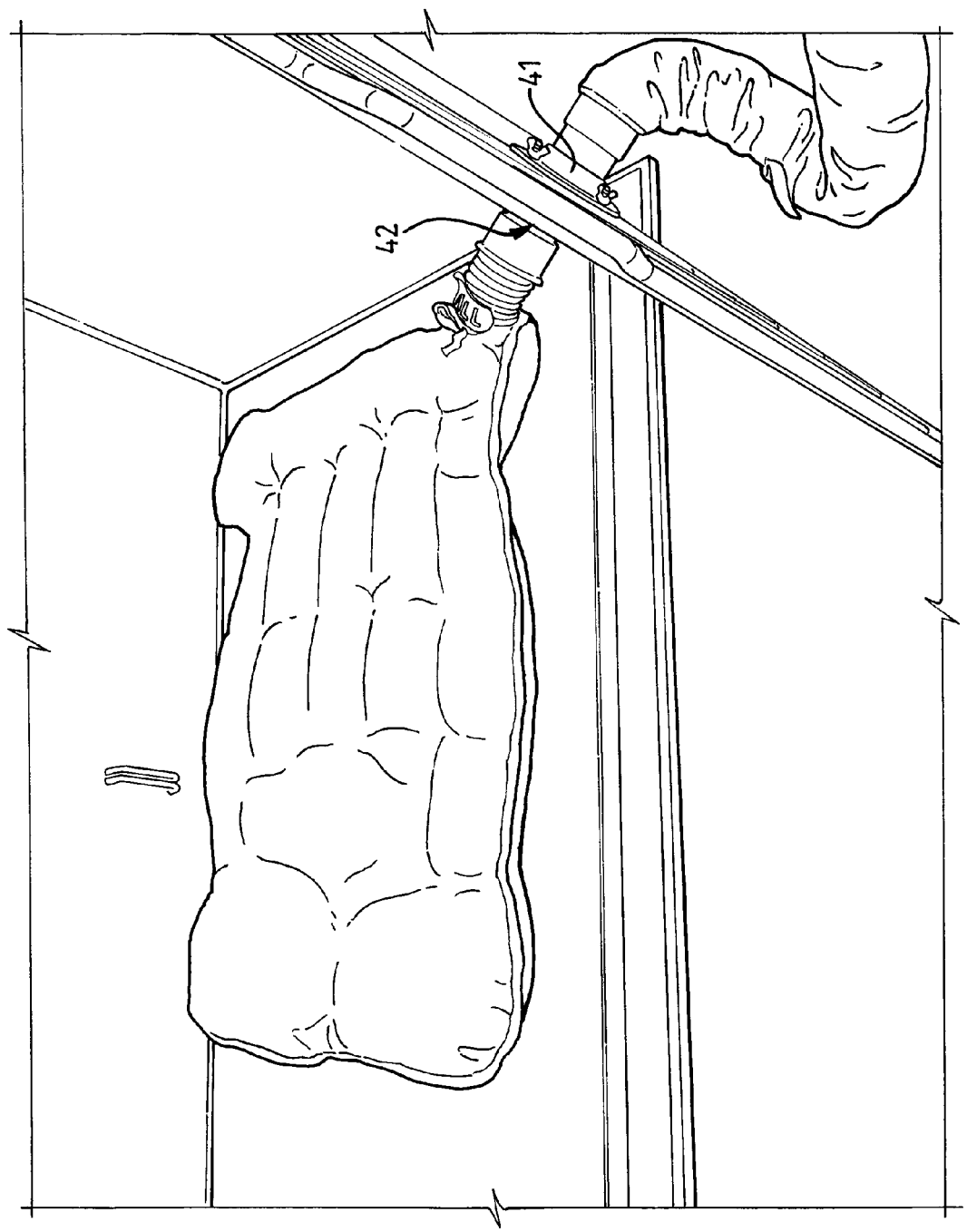
FIG. 9 shows the apparatus of FIGS. 6 to 8 connected to a blanket arrangement in accordance with an embodiment of the present invention.

FIG. 5 illustrates a blanket 2 which is equivalent to the embodiment of FIG. 3, shown not inflated.

Figure 4:
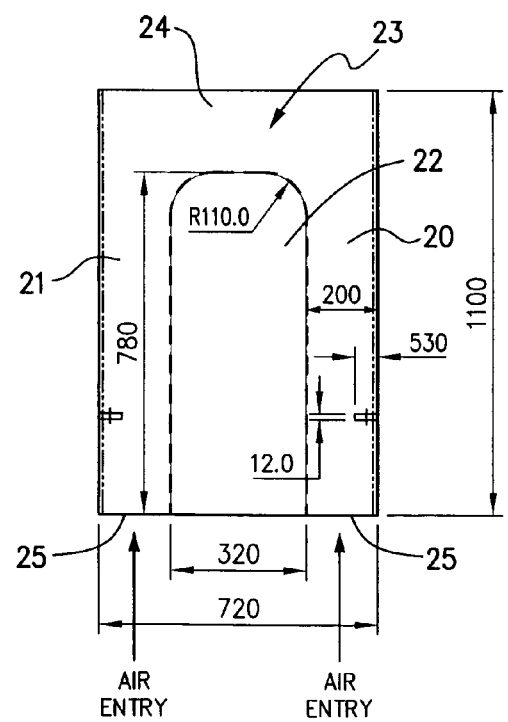
FIG. 4 is a diagram of a blanket arrangement in accordance with yet a further embodiment of the present invention.

FIG. 4 illustrates an embodiment of a blanket arrangement which is particularly designed to be used underneath the patient. In this embodiment, a pair of inflatable arms 20, 21 surround a patient receiving space 22 of the blanket 23. The arms 20, 21 are joined by an inflatable top section 24. The patient receiving space includes a base of polyester material which is a single sheet or a double sheet which is not inflatable. Air entry ports 25 are provided at each end of each arm 20, 21 of the "U" shaped arrangement.

In operation, air is introduced into one of the ports 25 and inflates the "U" shaped arrangement comprising arms 20, 21 and connecting top section 24. In this embodiment, the upper surface of the arms, 20, 21 and head section 24 are porous, to allow warm air to be introduced to the patient receiving space 22.

Figure 10:
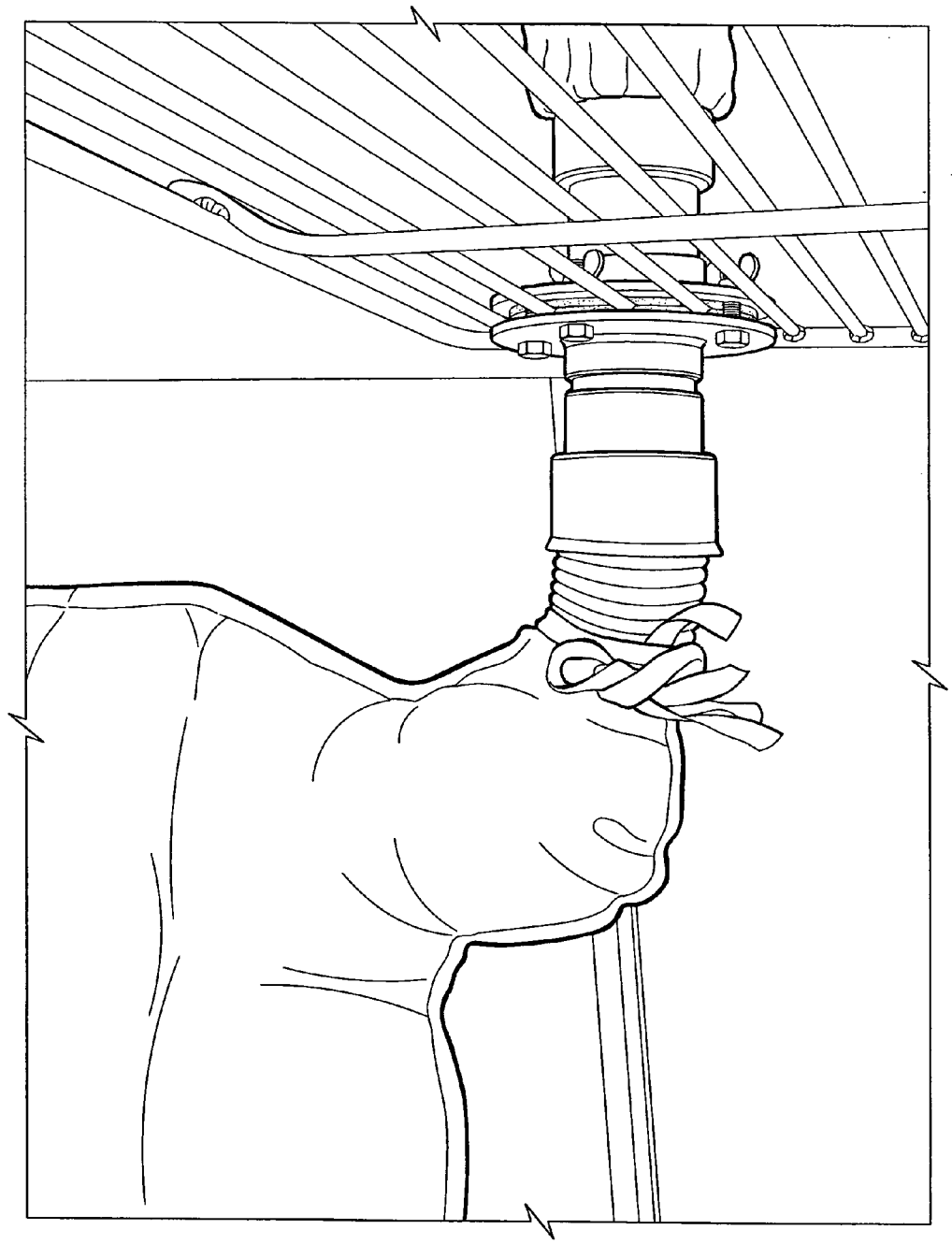
FIG. 10 shows a picture of an apparatus in accordance with the embodiment of FIGS. 6 to 8, shown connected to a blanket arrangement in accordance with an embodiment of the present invention.
Figure 12:
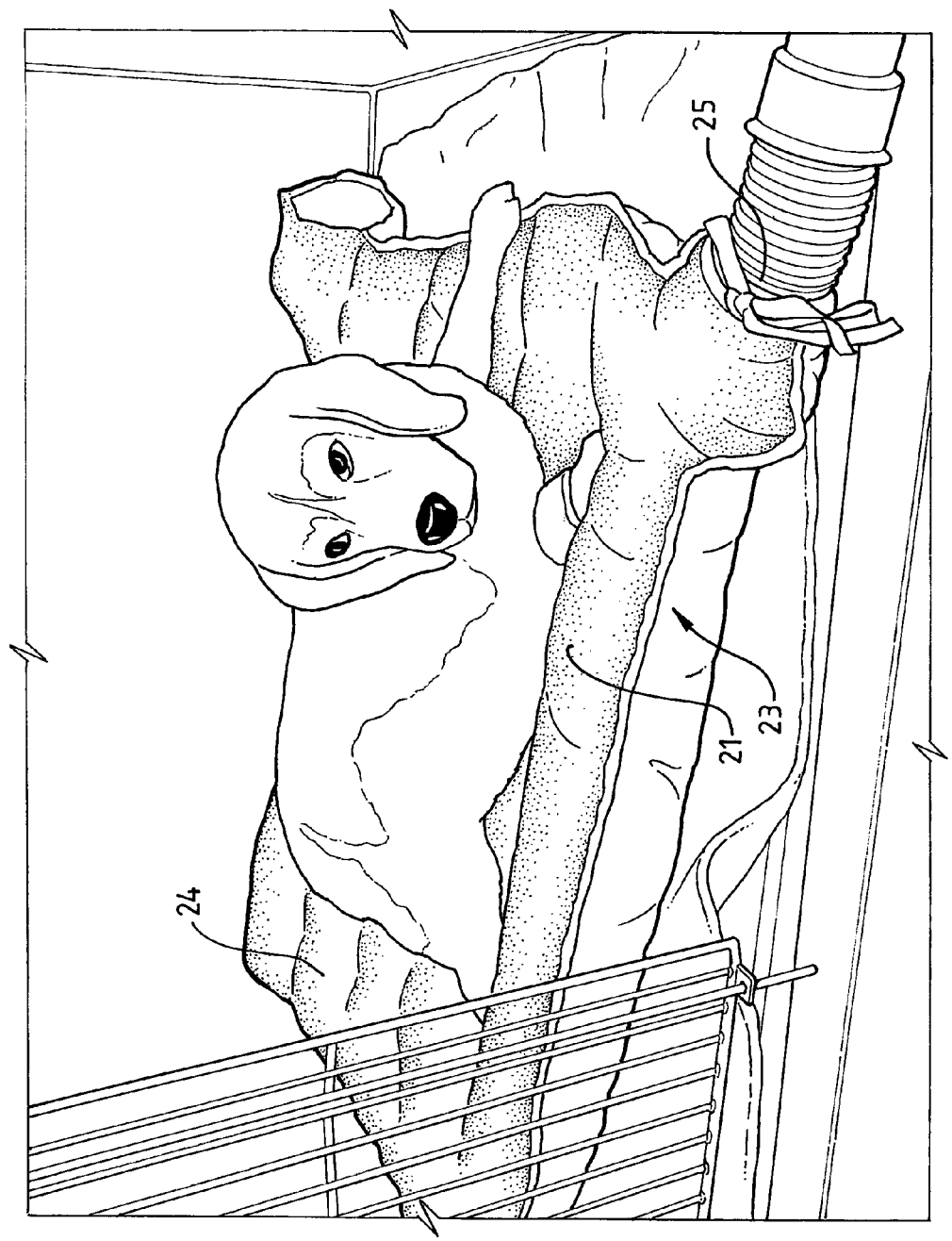
FIG. 12 shows a blanket arrangement of another embodiment of the present invention and apparatus in accordance with an embodiment of the present invention being used for treatment of a patient.

An embodiment of this blanket is pictured in operation in FIGS. 12 and 10.

Referring to FIGS. 6 through 10, a description will now be given of an apparatus for facilitating delivery of warmed air across a barrier (in this embodiment being a cage door) in accordance with an embodiment of the invention.

The apparatus comprises a first duct part 41 and a second duct part 42 (in this example the first part is outside of the cage door and the second part is intended inside the cage door). In this embodiment the first duct part 41 and second duct part 42 are provided by plastic sleeve portions 41, 42 which define ports 43, 44 of a duct.

A mounting mechanism, in this embodiment comprising bolts 46 and nuts 47 (a plurality of them) are arranged to mount the first part 41 on one side of the cage door 3 and the second part 42 on the other side of a cage door 3, opposite to each other, to provide a duct, 43, 44 for delivering air into the cage through the cage door 3.

The mounting mechanism 46, 47 is a fastening means which fastens the first part 41 and the second part 42 to each other, against the bars of the cage. It will be appreciated that the gauge of the bar spacing is irrelevant. The bars could even comprise a mesh, as long as the bolts 46 could project through the mesh.

The fasting mechanism is not limited to a nuts and bolts arrangement, but could be any arrangement for fastening the first part 41 and second part 42 together with the bars of the cage door 3. For example, it could comprise an adhesive to adhere the parts 41 and 42 to the cage bars. It could comprise clips clipping the part 41 and part 42 together through the cage bars. It could comprise other mechanisms.

The apparatus 1 in this embodiment also comprises a sealing arrangement 50, which comprises a first sealing member 51 and a second sealing member 52 mounted on the first duct part 41 and second duct part 42, respectively. In this example, the sealing members 51 and 52 comprise open cell foam rings fixed around the ports 43, 44 forming the duct. When the parts 41 and 42 are mounted, the foam 51 and 52 compresses around the cage door 3 bars and provides a reasonable seal maintaining the ducting of air flow through the cage door 3 within the conduit.

In an alternative embodiment, only a single sealing member 51 or 52 may be required mounted on one only of the first or second duct parts 41, 42. For example, a single open cell ring mounted on one of the duct parts may be sufficient to provide a seal across the barrier to the other duct part. Two sealing members 51 and 52 may, therefore, not be essential.

The ports 43 and 44 also provide connectors for connecting the conduit part 6 (outside the cage) and the further conduit 7 (inside the cage). In this embodiment, the ports form sleeve portions 43 and 44 which form socket connectors.

The conduit 6 includes a socket connector 60 arranged to mate with the socket connector formed by the sleeve portion 43 of the first part 41. The rest of the conduit 6 is formed by a flexible hose 61.

Inside the cage, the conduit 7 is formed from a further socket connector 62, arranged to mate with the socket connector formed by the sleeve portion 44 of part 42. The rest of the conduit 7 is formed by a flexible hose 63.

In this embodiment the arrangement is such that the diameter of the conduit 6, 7 varies only a little via the ducting apparatus 1, so as to minimize resistance to air flow.

The first duct part 41 and second duct part 42 also comprise flange portions 70 and 71 which face each other and mount the sealing arrangement 50 when mounted to the cage door 3. Flange portions 70, 71 allow plenty of room for the fastening mechanism, such as nuts 46 and bolts 47. The flanges 70 and 71 also allow plenty of room to mount the foam portions 51, 52.

Note that the sealing arrangement is not limited to an open cell foam, but could be any flexible membrane which can form around the bars of a cage. In some circumstances, there need not even be a complete seal, but a partial seal will suffice.

Note that in this embodiment, there are no fastening devices on the animal side of the cage that protrude substantially (just bolt heads of the bolts 46). This means there are limited sharp projections for the animal to injure themselves.

The apparatus 1 can be dismantled quite quickly, as can be seen, so the first part 41, for example, could be moved, together with conduit 6 quickly to another cage to mate with another second part 42 so that warmed air can be delivered to the other cage.

As also can be seen, the doors of the cage 4 can be open and shut relatively easily with little movement of the blanket 2.

Figure 11:
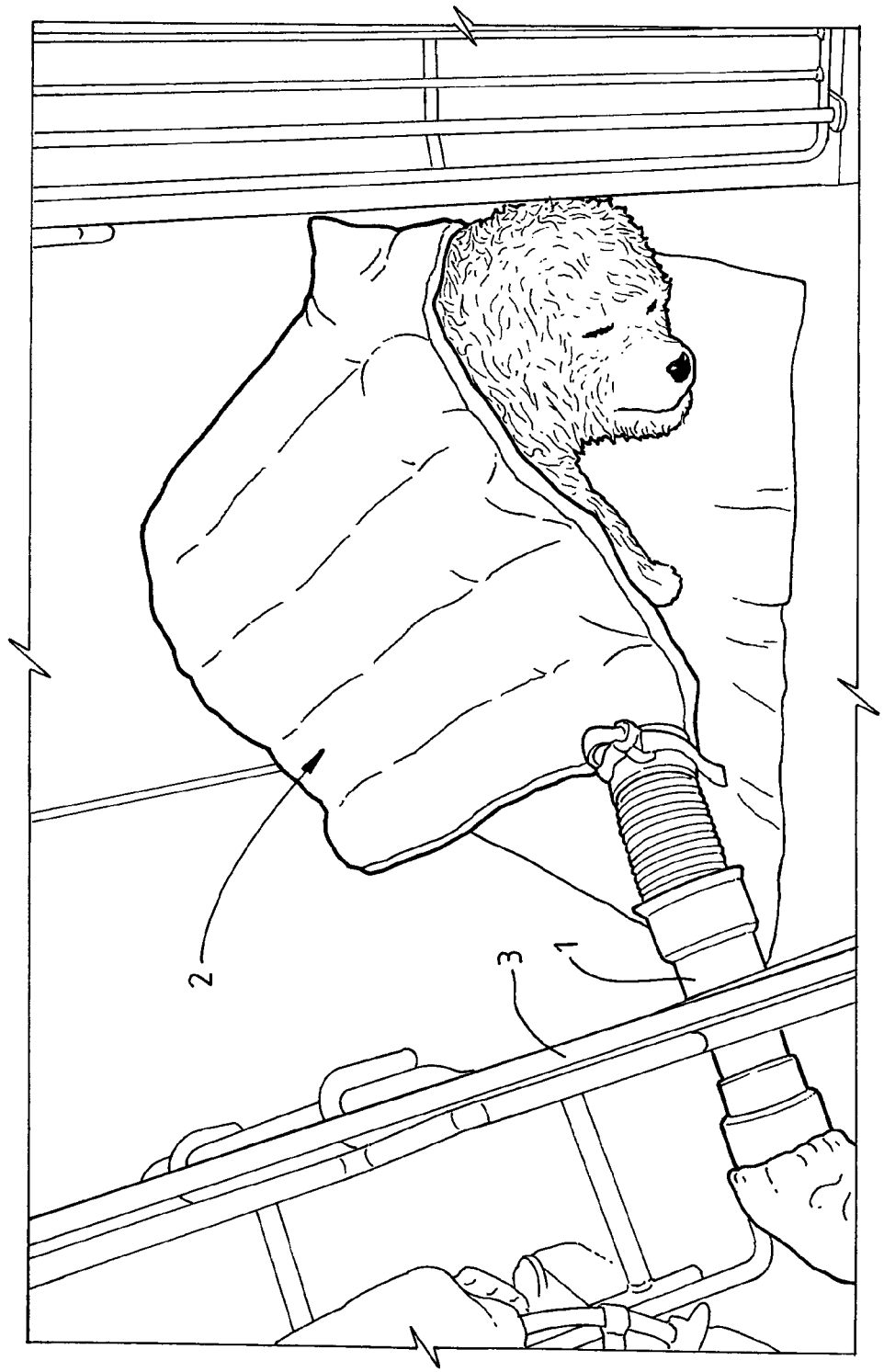
FIG. 11 shows a blanket arrangement and apparatus in accordance with an embodiment of the present invention being used for treatment of a patient.

FIG. 11 shows a picture of a patient with a blanket 2 laying, over the patient and an apparatus 1 delivering air to the blanket via the cage door 3.

In another embodiment, further conduits 7 on the inside of the cage may not be formed by a separate socket connector 62 of flexible hose 63, but may instead be formed by extended walls of the port 8, the extended walls forming a conduit which may be directly tied around the second duct part 42. All this requires is the walls which form the ports be extended so that they can form a conduit. The walls of the port may be provided with reinforcing or elastic or a tie to tie around the second duct part 42. In an embodiment, the second duct part 42 may include a circumferential groove within which the tie can be seated when the conduit (extension of the port from the blanket) is tied off. The second duct part 42 may have a rounded edge to prevent animals injuring themselves.

Figure 13:
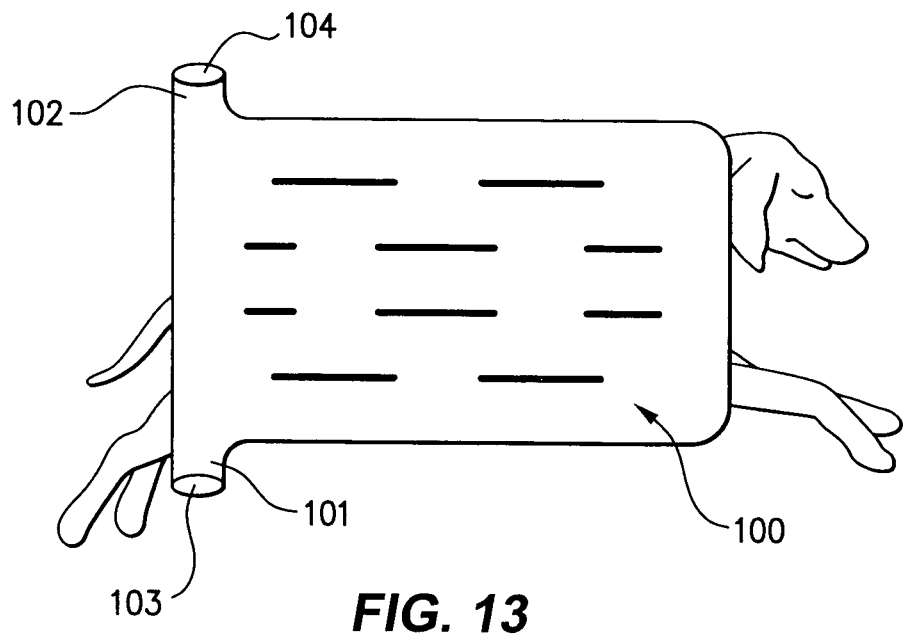
FIG. 13 is a diagram of a blanket arrangement in accordance with a further embodiment of the present invention.

FIG. 13 shows a further embodiment of a blanket in accordance with the present invention, designated reference numeral 100. The blanket includes a pair of limbs 101, 102 which extends substantially transversely to the longitudinal direction of the blanket 100, and within the ends of which ports 103, 104 are formed. The length of the limbs 101, 102 is such that they can operate as the further conduit, and the ports 103, 104 can be directly tied around the second duct part.

Figure 14:
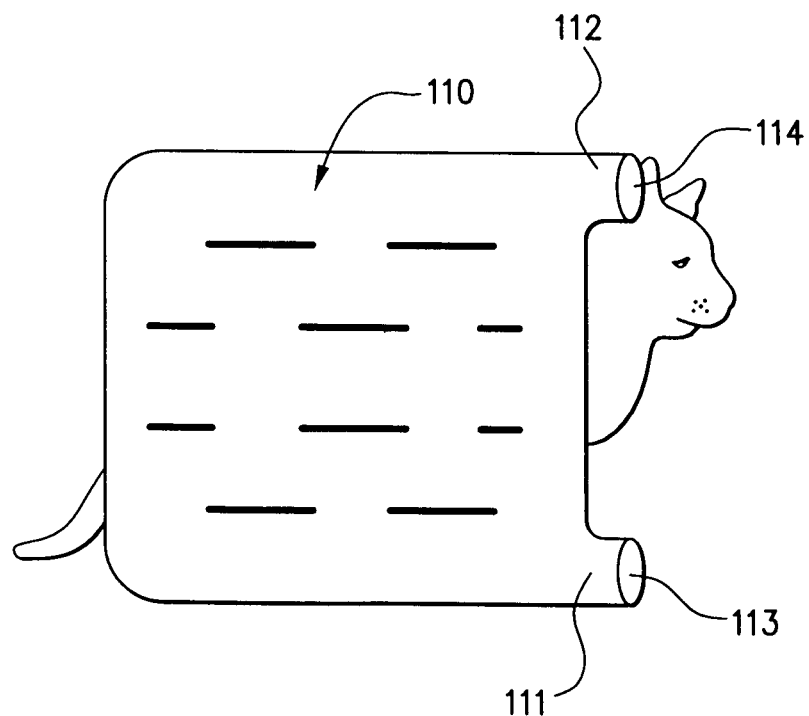
FIG. 14 is a diagram of a blanket arrangement in accordance with an embodiment of the invention.

A blanket for a smaller animal cage is shown in FIG. 14, generally designated by reference numeral 110. The limbs defining the ports extend in a direction parallel to the longitudinal direction of the blanket. The limbs 111, 112 are of sufficient length that they can operate as further conduits and the ports 113, 114 can be tied directly around the second duct part.

Having blankets with the port "limbs" designed long enough to connect to the second duct part obviates the needs for a second, separate extension conduit on the animal side of the cage door. Further, the extension may be long enough so that the cage door can be opened or closed without "dragging" the blanket off the animal. This means that the animal can be set up with the door open, then the door can be closed, then opened again if it is required to check the animal, without disturbing the blanket orientation.

In the above embodiments, the system is shown being used with a cage for holding animals. The cage need not necessarily be of the form shown (barred doors at the front and solid sides, ceiling and base). The entire cage could be bars, for example. The walls could be glass, apart from the barred doors. Any other arrangement is possible. As discussed above, the bars may be replaced by mesh. In another embodiment, the door may be glass or plastics with a hole for the ducted air, the second part of the apparatus being mounted on the plastic around the hole and the first part being mounted on the other side of the plastics or glass.

In the above embodiments, the system is used to warm animals. In other embodiments it may be used to warm humans, e.g. infants, and the ducting apparatus may be used to duct air via the bars of a cot or the like, for example.

In the above embodiments, the system is used to provide warm air to the patient. In alternative embodiments it may be used to provide cool air, or any type of conditioned air.

In the above embodiments, the ducting apparatus is in the form of an adapter and connectors are also provided to connect to the warm air conduit. In an alternative embodiment, the warm air conduit may be integral with the first part and the further warm air conduit integral with the second part.

In the above embodiments, the conduit is cylindrical. It is not limited to a circular or oval shape, however, but could be any profile, e.g. rectilinear.

In the above embodiments, the first duct part 41 and the second duct part 42 are of the same configuration. They are therefore interchangeable. The apparatus is therefore easy to manufacture as it only requires one form of duct part. The invention is not limited to this, however, and each of the first and second duct parts could be of different configuration.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It will be understood to persons skilled in the art of the invention that many modifications may be made without departing from the spirit and scope of the invention.

What is claimed is:

1. An apparatus for facilitating delivery of conditioned air across a barrier to a blanket arrangement providing the conditioned air to a patient, the apparatus comprising a first duct part, a second duct part and a mounting mechanism, the mounting mechanism arranged to mount the first duct part on one side of the barrier and the second duct part on the other side of the barrier opposite the first duct part, to provide a duct for ducting conditioned air across the barrier irrespective of the arrangement of the barrier, the barrier comprising bars or mesh, and the apparatus further comprising a seal arrangement to provide at least a partial seal across the bars or mesh.

2. The apparatus in accordance with claim 1, further comprising a conduit arranged to provide the conditioned air and a further conduit across the barrier arranged for providing the conditioned air to the blanket arrangement, the apparatus being arranged to duct the air from the conduit to the further conduit.

3. The apparatus in accordance with claim 2, the first duct part comprising a connecting portion for releasably connecting to the conduit.

4. The apparatus in accordance with claim 2, the second duct part comprising a second connector portion for connecting to the further conduit.

5. The system in accordance with claim 2, wherein the further conduit is integral with the blanket arrangement.

6. The apparatus in accordance with claim 1, wherein the seal arrangement comprises a first seal portion mounted by the first duct part and a second seal portion mounted by the second duct part, the first and second seal portions arranged to make a seal across the barrier when the first and second duct parts are mounted on opposite sides of the barrier.

7. The apparatus in accordance with claim 1, wherein the mounting mechanism comprises a fastening mechanism for fastening the first and second duct parts to each other across the barrier.

8. The apparatus in accordance with claim 1, wherein the barrier is part of a cage for holding the patient.

9. The apparatus in accordance with claim 1, wherein the patient is an animal patient.

10. A system for providing conditioned air to a patient, comprising an apparatus in accordance with claim 1, and a blanket arrangement for receiving the conditioned air and providing it to the patient.

11. The apparatus in accordance with claim 10, further comprising a conditioning unit for providing conditioned air to the conduit.

12. An apparatus for facilitating delivery of conditioned air across a barrier to a blanket arrangement providing the conditioned air to a patient, the apparatus comprising a first duct part, a second duct part, and a mounting mechanism, the mounting mechanism arranged to mount the first duct part on one side of the barrier and the second duct part on the other side of the barrier opposite the first duct part, to provide a duct for ducting conditioned air across the barrier, and a blanket arrangement for receiving the conditioned air and providing it to the patient.

* * * * *